United States Patent [19]

Roch et al.

[11] Patent Number: 4,560,685

[45] Date of Patent: Dec. 24, 1985

[54] 2-PIPERAZINO-PTERIDINES USEFUL AS ANTITHROMBOTICS AND ANTIMETASTATICS

[75] Inventors: Josef Roch; Josef Nickl; Erich Müller; Berthold Narr; Johannes Weisenberger, all of Biberach; Rainer Zimmermann, Mittelbiberach; Walter Haarmann, Biberach, all of Fed. Rep. of Germany

[73] Assignee: Dr. Karl Thomae Gesellschaft mit beschränkter Haftung, Ingelheim am Rhein, Fed. Rep. of Germany

[21] Appl. No.: 621,438

[22] Filed: Jun. 18, 1984

[51] Int. Cl.[4] .................. A61K 31/505; C07D 475/08
[52] U.S. Cl. .................... 514/222; 514/232; 514/237; 514/239; 514/249; 544/58.2; 544/61; 544/81; 544/118; 544/260
[58] Field of Search ............... 544/58.2, 61, 81, 118, 544/260; 424/246, 248.4, 248.52, 248.56, 248.57, 248.58, 251; 514/222, 232, 237, 239, 249

[56] References Cited

U.S. PATENT DOCUMENTS

| | | | |
|---|---|---|---|
| 2,940,972 | 6/1960 | Roch | 544/118 X |
| 3,159,628 | 12/1964 | Pachter et al. | 544/81 X |
| 3,487,082 | 12/1969 | Cragoe et al. | 544/260 |
| 3,859,287 | 1/1975 | Parish et al. | 544/260 |

Primary Examiner—Richard L. Raymond
Attorney, Agent, or Firm—Hammond & Littell, Weissenberger & Dippert

[57] ABSTRACT

Compounds of the formula

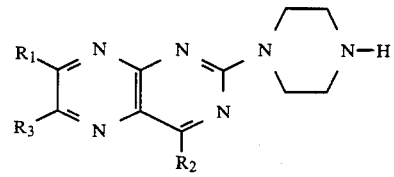

wherein
 $R_1$ is phenylalkylamino, alkylamino, dialkylamino, piperidino, morpholino, thiomorpholino or 1-oxido-thiomorpholino;
 $R_2$ is dialkylamino, piperidino, morpholino, thiomorpholino or 1-oxido-thiomorpholino; and
 $R_3$ is halogen, alkoxy, alkylthio, phenylalkoxy or phenylalkylthio;

and non-toxic, pharmacologically acceptable acid addition salts thereof. The compounds as well as their salts are useful as antithrombotics and antimetastatics.

9 Claims, No Drawings

2-PIPERAZINO-PTERIDINES USEFUL AS ANTITHROMBOTICS AND ANTIMETASTATICS

The present invention relates to novel 2-piperazinopteridines and non-toxic acid addition salts thereof, to methods of preparing these compounds, to pharmaceutical compositions containing them as active ingredients, and to a method of using them as antithrombotics and antimetastatics.

More particularly, the present invention relates to a novel class of compounds represented by the formula

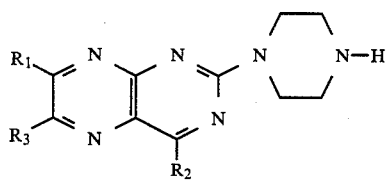

wherein
$R_1$ is [phenyl(alkyl of 1 to 3 carbon atoms)]amino, (alkyl of 1 to 3 carbon atoms)amino, di(alkyl of 1 to 3 carbon atoms)amino, piperidino, morpholino, thiomorpholino or 1-oxido-thiomorpholino;
$R_2$ is di(alkyl of 1 to 3 carbon atoms)amino, piperidino, morpholino, thiomorpholino or 1-oxido-thiomorpholino; and
$R_3$ is halogen, alkoxy of 1 to 3 carbon atoms, (alkyl of 1 to 3 carbon atoms)thio, phenyl(alkoxy of 1 to 3 carbon atoms) or phenyl(alkyl of 1 to 3 carbon atoms)thio;
and non-toxic, pharmacologically acceptable acid addition salts thereof.

Examples of specific embodiments of substituents $R_1$, $R_2$ and $R_3$ are the following:

$R_1$: methylamino, ethylamino, propylamino, isopropylamino, benzylamino, (1-phenylethyl)amino, (2-phenylethyl)amino, (3-phenylpropyl)amino, dimethylamino, diethylamino, dipropylamino, N-methyl-ethylamino, piperidino, morpholino, thiomorpholino or 1-oxidothiomorpholino;

$R_2$: dimethylamino, diethylamino, dipropylamino, diisopropylamino, N-methyl-ethylamino, N-ethyl-propylamino, piperidino, morpholino, thiomorpholino or 1-oxidothiomorpholino;

$R_3$: chlorine, bromine, methoxy, ethoxy, propoxy, isopropoxy, benzyloxy, 1-phenylethoxy, 2-phenylethoxy, 1-phenylpropoxy, 2-phenylpropoxy, 3-phenylpropoxy, 1-methyl-2-phenylethoxy, methylmercapto, ethylmercapto, propylmercapto, isopropylmercapto, benzylmercapto, (1-phenylethyl)mercapto, (2-phenylethyl)mercapto or (3-phenylpropyl)mercapto.

A preferred subgenus is constituted by those compounds of the formula I
wherein
$R_1$ is dimethylamino, benzylamino, piperidino, morpholino, thiomorpholino or 1-oxido-thiomorpholino;
$R_2$ is dimethylamino, piperidino, morpholino, thiomorpholino or 1-oxidothiomorpholino, and
$R_3$ is chlorine, bromine, alkoxy of 1 to 3 carbon atoms, (alkyl of 1 to 3 carbon atoms)mercapto, benzyloxy or benzylmercapto;
and non-toxic, pharmacologically acceptable acid addition salts thereof.

A particularly preferred subgenus is constituted by those compounds of the formula I,
wherein
$R_1$ is benzylamino, dimethylamino, morpholino, thiomorpholino or 1-oxido-thiomorpholino;
$R_2$ is dimethylamino, morpholino, thiomorpholino or 1-oxido-thiomorpholino; and
$R_3$ is chlorine, alkoxy of 1 to 3 carbon atoms, (alkyl of 1 to 3 carbon atoms)mercapto, benzyloxy or benzylmercapto;
and non-toxic, pharmacologically acceptable acid addition salts thereof.

The compounds embraced by formula I may be prepared by the following methods:
Method A:
For the preparation of those compounds of the formula I wherein $R_1$ is halogen, by reacting a compound of the formula

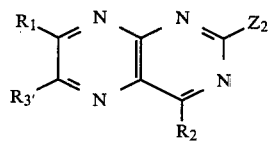

wherein
$R_1$ and $R_2$ have the meanings previously defined,
$R_3$ is halogen, and
$Z_2$ is a nucleophilically exchangeable group such as a halogen atom, for example chlorine or bromine atom, with a piperazine of the formula

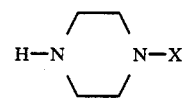

wherein X is hydrogen or a hydrolytically removable protective group and, if necessary, subsequently splitting off the protective group.

The reaction is advantageously carried out in a solvent such as tetrahydrofuran, dioxane, benzene, toluene or dimethylglycol ether, at temperatures between 50° and 150° C., preferably at the boiling point of the solvent or with the reactants in the molten state. It may be advantageous to use an acid-binding agent such as sodium carbonate, triethylamine or pyridine.

If it is necessary to split off a protective group, this may be done in the presence of an acid such as hydrochloric or sulfuric acid or of a base such as sodium hydroxide or potassium hydroxide, preferably in an aqueous solvent such as methanol/water, ethanol/water or dioxane/water, and at temperatures up to the boiling point of the solvent.
Method B:
For the preparation of a compound of the formula I wherein $R_3$ is alkoxy, alkylmercapto, phenylalkoxy or phenylalkylmercapto, by reacting a compound of the formula

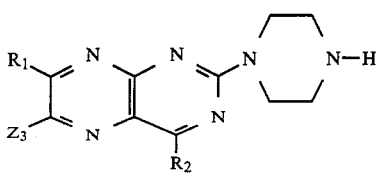

(IV)

wherein
R₁ and R₂ have the meanings previously defined, and
Z₃ is a nucleophilically exchangeable substituent such as a halogen atom, for instance a chlorine or bromine atom, with a compound of the formula $$R_3'—H \qquad (V)$$

wherein
$R_3'$ is alkoxy of 1 to 3 carbon atoms, (alkyl of 1 to 3 carbon atoms)mercapto, phenyl(alkoxy of 1 to 3 carbon atoms) or phenyl(alkyl of 1 to 3 carbon atoms)mercapto,
or an alkali metal salt thereof.

The reaction is preferably carried out in a suitable solvent such as dioxane, tetrahydrofuran, methanol, ethanol propanol, isopropanol or benzyl alcohol and in the presence of an alkali metal salt of a compound of the formula V, for instance sodium methoxide, sodium ethoxide or sodium benzylmercaptide, at temperatures between 50° and 150° C., for example at the boiling point of the solvent.

The compounds of the formula I are basic and therefore form addition salts with inorganic or organic acids. Examples of non-toxic, pharmacologically acceptable acid addition salts are those formed with hydrochloric, hydrobromic, sulfuric, phosphoric, lactic, citric, tartaric, succinic, maleic or fumaric acid.

The starting compounds of the formulas II to V are largely known or may be obtained by the process described in U.S. Pat. No. 2,940,972 (see Examples A to C below).

The following examples illustrate the present invention and will enable others skilled in the art to understand it more completely. It should be understood, however, that the invention is not limited solely to the particular examples given below.

Preparation of starting compounds:

EXAMPLE A 2,6,7-Trichloro-4-morpholino-pteridine

A solution of 4.35 g (0.05 mol) of morpholine in 100 ml of chloroform was slowly added dropwise to a mixture of a suspension of 13.5 g (0.05 mol) of 2,4,6,7-tetrachloropteridine in about 400 ml of chloroform and a solution of 10 g (0.1 mol) of potassium bicarbonate in 100 ml of water, while vigorously stirring and cooling to −5° to 0° C., and the resulting mixture was stirred for 30 minutes more while cooling. The chloroform phase containing the reaction product was separated, dried over sodium sulfate and evaporated in vacuo.

Yield: 13.5 g (84% of theory). Melting point: 211°–213° C. (ethyl acetate).

The following compounds were prepared in analogy to Example A:

2,6,7,-Trichloro-4-thiomorpholino-pteridine, Melting point: 191°–193° C.

2,6,7-Trichloro-4-(1-oxido-thiomorpholino)pteridine, Melting point: 212°–214° C. (decomposition).

EXAMPLE B 2,6-Dichloro-4,7-bis-(1-oxido-thiomorpholino)pteridine

A solution of 23.8 g (0.2 mol) of thiomorpholine-1-oxide in 100 ml of dioxane was slowly added to a solution of 13.5 g (0.05 mol) of 2,4,6,7-tetrachloro-pteridine in 300 ml of dioxane, while stirring, at room temperature, whereupon a yellowish precipitate was rapidly formed. The reaction mixture was taken up in about 2 liters of water. After standing for some time, the reaction product which precipitated was suction-filtered off, washed with water and dried at about 70° C.

Yield: 19.2 g (88% of theory). Melting point: 237°–239° C. (ethanol).

The following compounds were prepared in analogy to Example B:

2,6-Dichloro-4,7-dimorpholino-pteridine, Melting point: 206°–208° C.

2,6-Dichloro-4,7-bis-(thiomorpholino)-pteridine, Melting point: 193°–195° C. (from dioxan).

2,6-Dichloro-4,7-bis(dimethylamino)-pteridine, Melting point: 245°–247° C.

2,6-Dichloro-4,7-dipiperidino-pteridine, Melting point: 185°–187° C.

EXAMPLE C

7-Benzylamino-2,6-dichloro-4-morpholino-pteridine

A solution of 7 g (0.065 mol) of benzylamine in 50 ml of dioxane was slowly added to a suspension of 9.6 g (0.03 mol) of 2,6,7-trichloro-4-morpholino-pteridine in about 150 ml of dioxane at room temperature while stirring. After stirring for about one hour, the reaction mixture was taken up in about 1 liter of water. The precipitate which formed after standing for some time was suction-filtered off, washed with water and dried at 60° C.

Yield: 10.9 g (94% of theory). Melting point: 213°–214° C. (ethanol/dioxane=2:1).

The following compounds were prepared in analogy to Example C:

7-Benzylamino-2,6-dichloro-4-(1-oxido-thiomorpholino)-pteridine. Melting point: 253°–254° C.

2,6-Dichloro-7-morpholino-4-(1-oxido-thiomorpholino)-pteridine. Melting point: 215°–217° C.

2,6-Dichloro-4-morpholino-7-(1-oxido-thiomorpholino)-pteridine. Melting point: 218°–220° C.

Preparation of end products of the formula I:

EXAMPLE 1

6-Chloro-4,7-dimorpholino-2-piperazino-pteridine 9.3 g (0.025 mol) of 2,6-dichloro-4,7-dimorpholino-pteridine were refluxed for one hour with 8.6 g (0.1 mol) of anhydrous piperazine in 200 ml of dioxane. The solvent was substantially distilled off, and the residue was digested with about 100 ml of water. After the aqueous mixture stood for a short time, it was suction-filtered, and the filter cake was washed with water and dried at about 70° C.

Yield: 8.9 g (85% of theory). Melting point: 220°–222° C. $C_{18}H_{25}ClN_8O_2$ (420.9). Calculated: C-51.36%; H-5.99%; Cl-8.42%; N-26.62% Found: C-51.21%; H-5.97%; Cl-8.48%; N-26.68%.

EXAMPLE 2

6-Benzylthio-4,7-dimorpholino-2-piperazino-pteridine

A solution of 0.35 g of sodium and 2 ml (about 0.017 mol) of benzylmercaptan in 100 ml of dioxane was added to a solution of 6.3 g (0.015 mol) of 6-chloro-4,7-dimorpholino-2-piperazino-pteridine in 200 ml of dioxane, and the resulting mixture was refluxed for about 2 hours. The solvent was substantially distilled off in vacuo and the residue was taken up in about 200 ml of water. After it had solidified, the reaction product was suction-filtered off, washed with water and dried in vacuo at room temperature.

Yield: 6.4 g (84% of theory).

After purification on a silicagel column (eluant: methanol/conc. ammonia; 50:1) and recrystallization from ethyl acetate, the substance melted at 135°–137° C.

$C_{25}H_{32}N_8O_2S$ (508.7) Calculated: C-59.03%, H-6.34%; N-22.03%; S-6.30%; Found: C-59.28%; H-6.55%; N-22.19%; S-6.36%.

EXAMPLE 3

7-Benzylamino-6-methoxy-4-(1-oxido-thiomorpholino)-2-piperazino-pteridine

A solution of 0.23 g (0.01 mol) of sodium in 10 ml of methanol was poured into a solution of 2.9 g (0.006 mol) of 7-benzylamino-6-chloro-4-(1-oxido-thiomorpholino)-2-piperazino-pteridine in 100 ml of dioxane. The resulting mixture was refluxed for 30 minutes and then the solvent was substantially distilled off in vacuo. The residue was taken up in about 70 ml of water, and the reaction product which precipitated was suction-filtered off, washed with water and dried at about 60° C.

Yield: 2.6 g (93% of theory).

After reprecipitation from 0.1N hydrochloric acid using ammonia, and recrystallization from ethyl acetate/methanol (4:1), the compound melted at 148°–151° C.

$C_{22}H_{28}N_8O_2S$ (468.6). Calculated: C-56.39%; H-6.02%; N-23.91%; S-6.84%. Found: C-56.61%; H-6.27%; N-23.40%; S-6.44%.

EXAMPLE 4

6-Chloro-4-morpholino-7-(1-oxido-thiomorpholino)-2-piperazino-pteridine

This compound was prepared analogous to Example 1 from 2,6-dichloro-4-morpholino-7-(1-oxido-thiomorpholino)pteridine and piperazine.

Melting point: 225°–227° C. (precipitation from 0.1N HCl by means of ammonia).

EXAMPLE 5

6-Chloro-4,7-bis-(1-oxido-thiomorpholino)-2-piperazino-pteridine

This compound was prepared analogous to Example 1 from 2,6-dichloro-4,7-bis-(1-oxido-thiomorpholino)pteridine and piperazine.

Melting point: >200° C. (decomposition).

EXAMPLE 6

6-Chloro-4,7-dipiperidino-2-piperazino-pteridine

This compound was prepared analogous to Example 1 from 2,6-dichloro-4,7-dipiperidino-pteridine and piperazine.

Melting point: decomposition at about 200° C.

EXAMPLE 7

6-Chloro-4,7-bis-(dimethylamino)-2-piperazino-pteridine

This compound was prepared analogous to Example 1 from 2,6-dichloro-4,7-bis(dimethylamino)pteridine and piperazine.

Melting point: 130°–134° C.

EXAMPLE 8

6-Chloro-2-piperazino-4,7-bis-(thiomorpholino)pteridine

This compound was prepared analogous to Example 1 from 2,6-dichloro-4,7-bis-(thiomorpholino)pteridine and piperazine.

Melting point: 194°–196° C. (ethyl acetate).

EXAMPLE 9

6-Chloro-7-morpholino-4-(1-oxido-thiomorpholino)-2-piperazino-pteridine

This compound was prepared analogous to Example 1 from 2,6-dichloro-7-morpholino-4-(1-oxido-thiomorpholino)pteridine and piperazine.

Melting point: >240° C. (decomposition).

EXAMPLE 10

7-Benzylamino-6-chloro-4-morpholino-2-piperazino-pteridine

This compound was prepared analogous to Example 1 from 7-benzylamino-2,6-dichloro-4-morpholino-pteridine and piperazine.

Melting point: 195°–197° C. (methanol/water).

EXAMPLE 11

7-Benzylamino-6-chloro-4-(1-oxido-thiomorpholino)-2-piperazino-pteridine

This compound was prepared analogous to Example 1 from 7-benzylamino-2,6-dichloro-4-(1-oxido-thiomorpholino)pteridine and piperazine.

Melting point: >200° C. (decomposition).

EXAMPLE 12

6-Benzylthio-4,7-bis-(dimethylamino)-2-piperazino pteridine

This compound was prepared analogous to Example 2 from 6-chloro-4,7-bis-(dimethylamino)-2-piperazino-pteridine and benzylmercaptan.

Melting point: 150°–152° C.

EXAMPLE 13

7-Benzylamino-6-methylthio-4-(1-oxido-thiomorpholino)-2-piperazino-pteridine

This compound was prepared analogous to Example 2 from 7-benzylamino-6-chloro-4-(1-oxido-thiomorpholino)-2-piperazino-pteridine and methylmercaptan.

Melting point of the hydrochloride: 159°–162° C.

EXAMPLE 14

4-Morpholino-7-(1-oxido-thiomorpholino)-2-piperazino-6-propylthio-pteridine

This compound was prepared analogous to Example 2 from 6-chloro-4-morpholino-7-(1-oxido-thiomorpholino)-2-piperazino-pteridine and propylmercaptan.

Melting point: 125°–130° C.

EXAMPLE 15

7-Benzylamino-6-benzylthio-4-(1-oxido-thiomorpholino)-2-piperazino-pteridine

This compound was prepared analogous to Example 2 from 7-benzylamino-6-chloro-4-(1-oxido-thiomorpholino)-1-piperazino-pteridine and benzylmercaptan.

Melting point: >160° C. (decomposition).

EXAMPLE 16

6-Ethoxy-2-piperazino-4,7-bis-(thiomorpholino)-pteridine

This compound was prepared analogous to Example 3 from 6-chloro-2-piperazino-4,7-bis-(thiomorpholino)pteridine and ethanol.

Melting point: 147°–151° C.

EXAMPLE 17

6-Benzyloxy-4,7-bis-(dimethylamino)-2-piperazino-pteridine

This compound was prepared analogous to Example 3 from 6-chloro-4,7-bis-(dimethylamino)-2-piperazino-pteridine and benzyl alcohol.

Melting point: 166°–168° C.

EXAMPLE 18

6-Chloro-2-piperazino-4-dimethylamino-7-benzylamino-pteridine

This compound was prepared analogous to Example 1 from 2,6-dichloro-4-dimethylamino-7-benzylamino-pteridine and piperazine.

Melting point: 134°–137° C.

EXAMPLE 19

6-Chloro-2-piperazino-4-thiomorpholino-7-benzylamino-pteridine

This compound was prepared analogous to Example 1 from 2,6-dichloro-4-thiomorpholino-7-benzylamino-pteridine and piperazine.

Melting point: 160°–165° C.

EXAMPLE 20

6-Chloro-2-piperazino-4-thiomorpholino-7-dimethylamino-pteridine

This compound was prepared analogous to Example 1 from 2,6-dichloro-4-thiomorpholino-7-dimethylamino-pteridine and piperazine.

Melting point: 205°–207° C.

EXAMPLE 21

7-Benzylamino-6-benzylthio-2-piperazino-4-thiomorpholino-pteridine

This compound was prepared analogous to Example 2 from 7-benzylamino-6-chloro-2-piperazino-4-thiomorpholino-pteridine.

Melting point: from 70° C. (sintering).

The compounds of the present invention, that is, those embraced by formula I above and their non-toxic, pharmacologically acceptable acid addition salts, have useful pharmacodynamic properties. More particularly, they exhibit antithrombotic, antimetastatic and phosphodiesterase-inhibiting activities in warm-blooded animals.

The inhibiting effect of the compounds of the present invention on phosphodiesterase (PDE) from tumor cells and from human thrombocytes was ascertained in vitro, using the method described by Pöch et al. [see Naunyn-Schmiedebergs Arch. Pharmak. 268, 272–279 (1971)].

(a) Obtaining the enzyme:

The phosphodiesterase as obtained from B16 melanoma tissue from mice by centrifuging the homogenized tissue at 5000× g (for 15 minutes at 4° C.). The tissue was homogenized by repeated freezing/thawing and homogenizing according to Potter-Elvehjem or by ultrasound. The supernatant homogenate containing the PDE was deep-frozen in portions and deep-frozen at −25° C. The PDE was obtained analogously from human thrombocytes by freezing/thawing and centrifuging.

(b) Determining the PDE inhibition (PDE assay):

The PDE inhibition by the test substance was determined with 1 μmol/liter $^3$H-cAMP as substrate. The PDE inhibition was determined by measuring the degradation of the substrate $^3$H-cAMP to $^3$H-AMP by comparison with a control without any test substance. The $^3$H-AMP formed was separated off from the remaining $^3$H-cAMP by zinc sulfate/barium hydroxide precipitation.

The ED$_{50}$ was calculated, by linear regression analysis, as the concentration which inhibited PDE activity by 50%.

The following table shows the results obtained for a few representative species of the genus represented by formula I, where A=6-benzylthio-4,7-dimorpholino-2-piperazino-pteridine, B=6-chloro-4,7-bis(dimethylamino)-2-piperazino-pteridine, C=6-benzylthio-4,7-bis-(dimethylamino)-2-piperazino-pteridine, D=7-benzylamino-6-methylthio-4-(1-oxido-thiomorpholino)-2-piperazino-pteridine, and E=6-chloro-2-piperazino-4-dimethylamino-7-benzylamino-pteridine.

TABLE I

| Compound | PDE Inhibition (ED$_{50}$) | |
|---|---|---|
| | Thrombocytes | B16 Tumor cells |
| A | 0.051 | 0.088 |
| B | 35 | 0.95 |
| C | 10 | 0.88 |
| D | 0.048 | 0.97 |
| E | 14 | 0.37 |

Acute toxicity:

The approximate acute toxicity of the test compounds was determined on groups of 5 mice after oral administration of a single dose (observation period: 14 days).

TABLE II

| Compound | Approximate acute toxicity |
|---|---|
| A | >250 mg/kg (0 out of 5 animals died) |
| B | >250 mg/kg (0 out of 5 animals died) |
| C | >250 mg/kg (0 out of 5 animals died) |
| D | >250 mg/kg (0 out of 5 animals died) |
| E | >250 mg/kg (0 out of 5 animals died) |

By virtue of their pharmacodynamic properties the novel compounds of the present invention are useful for the prophylaxis of thromboembolic diseases such as coronary infarct, cerebral infarct, so-called transient ischaemic attacks and Amaurosis fugax, and for the prophylaxis of arteriosclerosis and metastasis.

For pharmaceutical purposes the compounds of the present invention are administered to warm-blooded animals perorally, parenterally or rectally as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups, suppositories and the like. An effective amount of the compounds of the present invention is from 0.1 to 4 mgm/kg body weight, preferably 0.2 to 3 mgm/kg body weight, two to four times daily.

The following examples illustrate a few pharmaceutical compositions comprising a compound of the present invention as an active ingredient and represent the best modes contemplated of using the invention. The parts are parts by weight unless otherwise specified.

EXAMPLE 22

Tablets

The tablet composition is compounded from the following ingredients:

| | |
|---|---|
| 6-Benzylthio-4,7-dimorpholino-2-piperazino-pteridine | 4.0 parts |
| Lactose | 23.0 parts |
| Corn starch | 14.5 parts |
| Polyvinylpyrrolidone | 4.0 parts |
| Magnesium stearate | 0.5 parts |
| Total | 50.0 parts |

Preparation:

The active ingredient, the lactose and the corn starch are intimately admixed with each other, and the mixture is moistened with an aqueous solution of the polyvinylpyrrolidone. The moist mass is passed through a 1 mm-mesh screen, the resulting granulate is dried, the dry granulate is again passed through the screen, the magnesium stearate is added, and the mixture is compressed into 5 mm-tablets. Each tablet contains 4 mg of the active ingredient.

EXAMPLE 23

Coated tablets

The tablets obtained in Example 22 are coated with a thin shell consisting essentially of a mixture of sugar and talcum.

EXAMPLE 24

Suppositories

The suppository composition is compounded from the following ingredients:

| | |
|---|---|
| 6-Benzylthio-4,7-dimorpholino-2-piperazine-pteridine | 25 parts |
| Suppository base (e.g. cocoa butter) | 1675 parts |
| Total | 1700 parts |

Preparation:

The suppository base is melted and cooled to 38° C. At that temperature the finely divided active ingredient is homogeneously dispersed therein, and 1700 mg-portions of the mixture are poured at 35° C. into chilled suppository molds and allowed to harden therein. Each suppository contains 25 mg of the active ingredient.

EXAMPLE 25

Aqueous suspension

The suspension is compounded from the following ingredients:

| | | |
|---|---|---|
| 6-Benzylthio-4,7-dimorpholino-2-piperazino-pteridine | 0.16 | parts |
| Carboxymethyl cellulose | 0.1 | parts |
| Methyl p-hydroxybenzoate | 0.05 | parts |
| Propyl p-hydroxybenzoate | 0.01 | parts |
| Cane sugar | 10.0 | parts |
| Glycerol | 5.0 | parts |
| 70% sorbitol | 20.0 | parts |
| Flavoring | 0.3 | parts |
| Distilled water ad | 100.0 | parts by vol. |

Preparation:

The distilled water is heated to 70° C. The methyl and propyl p-hydroxybenzoates, the glycerol and carboxymethyl cellulose are dissolved therein by stirring. The solution is cooled to room temperature and the active ingredient is added and homogeneously dispersed therein by stirring. After the sugar, sorbitol solution and flavoring have been added and dissolved, the suspension is evacuated to remove any air, while stirring. 5 ml of the suspension contains 8 mg of the active ingredient.

EXAMPLE 26

Hard gelatin capsules

The capsule filler composition is compounded from the following ingredients:

| | |
|---|---|
| 6-Benzylthio-4,7-dimorpholino-2-piperazino-pteridine | 150.0 parts |
| Dry corn starch | 180.0 parts |
| Powdered lactose | 87.0 parts |
| Magnesium stearate | 3.0 parts |
| Total | 320.0 parts |

Preparation:

The ingredients are admixed with each other, the mixture is passed through a 0.75 mm-mesh screen, the screened mixture is homogeneously mixed in a suitable apparatus, and 320 mg-portions are filled into No. 1 hard gelatin capsules. Each capsule contains 150 mg of the active ingredient.

Any one of the other compounds embraced by formula I or a non-toxic, pharmacologically acceptable acid addition salt thereof may be substituted for the particular active ingredient in Examples 22 through 26. Likewise, the amount of active ingredient in these illustrative examples may be varied to achieve the dosage unit range set forth above, and the amount and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

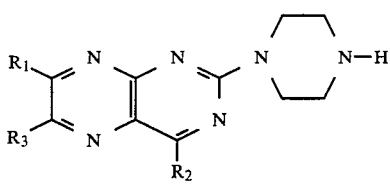

wherein
- R$_1$ is [phenyl(alkyl of 1 to 3 carbon atoms)]amino, (alkyl of 1 to 3 carbon atoms)amino, di(alkyl of 1 to 3 carbon atoms)amino, piperidino, morpholino, thiomorpholino or 1-oxido-thiomorpholino;
- R$_2$ is di(alkyl of 1 to 3 carbon atoms)amino, piperidino, morpholino, thiomorpholino or 1-oxido-thiomorpholino; and
- R$_3$ is halogen, alkoxy of 1 to 3 carbon atoms, (alkyl of 1 to 3 carbon atoms)thio, phenyl(alkoxy of 1 to 3 carbon atoms) or phenyl(alkyl of 1 to 3 carbon atoms)thio;

or a non-toxic, pharmacologically acceptable acid addition salt thereof.

2. A compound of claim 1,
where
- R$_1$ is dimethylamino, benzylamino, piperidino, morpholino, thiomorpholino or 1-oxido-thiomorpholino;
- R$_2$ is dimethylamino, piperidino, morpholino, thiomorpholino or 1-oxidothiomorpholino, and
- R$_3$ is chlorine, bromine, alkoxy of 1 to 3 carbon atoms, (alkyl of 1 to 3 carbon atoms)mercapto, benzyloxy or benzylmercapto;

or a non-toxic, pharmacologically acceptable acid addition salt thereof.

3. A compound of claim 1,
where
- R$_1$ is benzylamino, dimethylamino, morpholino, thiomorpholino or 1-oxido-thiomorpholino;
- R$_2$ is dimethylamino, morpholino, thiomorpholino or 1-oxido-thiomorpholino; and
- R$_3$ is chlorine, alkoxy of 1 to 3 carbon atoms or (alkyl of 1 to 3 carbon atoms)mercapto; benzyloxy or benzylmercapto;

or a non-toxic, pharmacologically acceptable acid addition salt thereof.

4. A compound of claim 1
where
- R$_1$ is benzylamino, dimethylamino, morpholino, or 1-oxido-thiomorpholino;
- R$_2$ is dimethylamino, morpholino or 1-oxido-thiomorpholino; and
- R$_3$ is chlorine, methylmercapto or benzylmercapto;

or a non-toxic, pharmacologically acceptable acid addition salt thereof.

5. A compound of claim 1, which is 6-benzylthio-4,7-dimorpholino-2-piperazino-pteridine or a non-toxic, pharmacologically acceptable acid addition salt thereof.

6. A compound of claim 1, which is 6-chloro-4,7-bis(dimethylamino)-2-piperazino-pteridine or a non-toxic, pharmacologically acceptable acid addition salt thereof.

7. A compound of claim 1, which is 6-benzylthio-4,7-bis(dimethylamino)-2-piperazino-pteridine or a non-toxic, pharmacologically acceptable acid addition salt thereof.

8. An antithrombotic or antimetastatic pharmaceutical composition consisting essentially of an inert pharmaceutical carrier and an effective antithrombotic or antimetastatic amount of a compound of claim 1.

9. The method of preventing or relieving thromboses or inhibiting metastases in a warm-blooded animal in need thereof, which comprises perorally, parenterally or rectally administering to said animal an effective antithrombotic or antimetastatic amount of a compound of claim 1.

* * * * *